United States Patent [19]

Andrade et al.

[11] 4,368,047
[45] Jan. 11, 1983

[54] PROCESS FOR CONDUCTING FLUORESCENCE IMMUNOASSAYS WITHOUT ADDED LABELS AND EMPLOYING ATTENUATED INTERNAL REFLECTION

[75] Inventors: Joseph D. Andrade; Richard Van Wagenen, both of Salt Lake City, Utah

[73] Assignee: University of Utah Research Foundation, Salt Lake City, Utah

[21] Appl. No.: 257,838

[22] Filed: Apr. 27, 1981

[51] Int. Cl.³ .................. G01N 33/54; G01N 31/06; G01N 21/64
[52] U.S. Cl. .................................. 435/4; 435/5; 435/7; 435/34; 436/517; 436/540; 436/546; 436/805; 436/815; 436/817; 436/816
[58] Field of Search .................. 424/8, 12; 435/7, 4, 435/5

[56] References Cited
U.S. PATENT DOCUMENTS 3,939,350  2/1976  Kronick .................... 424/12 X
4,050,895  9/1977  Hardy ...................... 23/230 R

OTHER PUBLICATIONS

E. S. West et al., "Textbook of Biochemistry", Fourth Edition, p. 342, Macmillan, New York, 1967.

*Primary Examiner*—Sidney Marantz
*Attorney, Agent, or Firm*—Thorpe, North & Western

[57] ABSTRACT

A process is presented for conducting fluorescence immunoassays without the use of added labels by utilizing ultraviolet radiation and internal reflection optics to activate fluorescent groups present in the molecules of interest. The assay is accomplished by directing a beam of light having wavelengths in the ultraviolet region to a solid liquid interface which (1) has a material X immobilized thereon, and (2) is contacted with an assay solution containing in unknown Y which contains intrinsic tyrosine, tryptophan, nucleic acid or related fluorescence groups which are activated by wavelengths in the ultraviolet region; X and Y may be in the relationship of antibody and antigen in that one had the ability of recognizing the particular spatial and polar configuration of the other and is attracted to and bound to such configuration, said beam of ultraviolet light being projected under such conditions that there is internal reflection at the interface, and then measuring the amount of fluorescence emitted from the surface of the interface, the amount of the fluorescence emission being a function of the amount of the unknown Y being detected. In the event that Y is not fluorescent, the X-Y sandwich can be further exposed to a solution containing X, to form XYX sandwich. The observed fluorescence of X is proportional to the amount of bound Y which is in turn related to the solution concentration of Y.

20 Claims, 3 Drawing Figures

TIME

PROCESS FOR CONDUCTING FLUORESCENCE IMMUNOASSAYS WITHOUT ADDED LABELS AND EMPLOYING ATTENUATED INTERNAL REFLECTION

There is a need in industry for methods that can be used to measure small quantities of naturally occurring and synthetic compounds or compositions. For example, there is a need for improved methods for detecting amounts of specific metabolic products, such as hormones, etc. as well as added materials, such as drugs, in the blood stream and in other body fluids and tissues.

These methods are broadly called immunoassays. Known methods depend on the ability of a receptor, usually an antibody, to recognize a particular spatial and polar configuration and bind to such configuration. As a result of this binding, the resulting complex can be differentiated from other molecules which are present but which are not bound to the specific receptor.

Various techniques have been proposed to effect the immunoassays. In one technique, referred to as radioimmunoassay, a ligand analog having radioactive atoms is added to the assay solution. By determining the distribution of radioactive labelled ligand between bound and unbound, one can determine the amount of ligand present in the unknown.

Another technique employs an enzyme as the detector. The technique can be carried out homogeneously or heterogeneously. In U.S. Pat. Nos. 3,654,090 and 3,791,932 heterogeneous systems are described. The heterogeneous system requires binding one of the reagents involved in the determination of a solid support, for example, the receptor. By allowing competition for the receptor bound to solid support between the ligand and ligand analog, and separating the solid support, one can then determine the enzyme activity in the supernatant. The amount of ligand analog remaining in the supernatant, as determined by the enzyme activity in the solution is related to the amount of unknown ligand present.

A third promising technique is a fluorescence immunoassay employing total reflection for activation, (U.S. Pat. No. 3,939,350). According to this process a nonfluorescent antibody is bound to the flat surface of an optically transparent sheet and the treated surface washed. The surface is then contacted with an aqueous solution containing the unknown and subjected to a second wash. The surface is then contacted with an aqueous solution containing an antibody which has ben tagged with a fluorescent group and subsequently washed. The interface so treated is then irradiated with light at the wave length of absorption of the fluorescent group bonded to the antibody. The angle of irradiation is selected to provide internal reflection so that fluorescence occurs only within a few thousand Angstroms of the surface. By measuring the amount of fluorescence, for example, with a photomultiplier tube, the amount of unknown present in the solution can be determined.

Each of the above systems have advantages and disadvantages as applied to specific situations. In one or more of the systems, expensive equipment is required. Working with radioactive materials is undesirable. Furthermore, the radioactive materials have only a limited shelf life. The enzyme technique is subject to interfering substances present in the unknown. The fluorescence immunoassay using reflection has advantages but also the shortcoming of multiple washing steps, the need for expensive secondary reagents such as materials labeled with a fluorescent probe which is excited and fluoresces in the visible region of the spectrum. In addition, this places a limitation on its use with some materials, such as low molecular weight hormones and proteins, which in some cases are perturbed in the interaction by the presence of the fluorescent label.

It is an object of the invention, therefore, to provide a new process for immunoassays using interfacial techniques which do not require the use of labels but possess the other advantages of the spectroscopic techniques. It is a further object to provide a new immunoassay process employing fewer operational steps, less expensive secondary reagents and is particularly suited for use with materials, such as proteins, hormones and drugs, which might be affected by the presence of the fluorescence and radioactive labels used in the prior known processes.

DESCRIPTION OF THE INVENTION

It has now been discovered that these and other objects can be accomplished by the process of the invention which conducts the fluorescence immunoassay without labels using internal reflection and wave lengths in the ultraviolet region. The assay is accomplished according to the present invention by directing a beam of light having wave lengths in the ultraviolet region to a solid-liquid interface which (1) has a material X immobilized thereon, and (2) is in contact with an aqueous solution containing an unknown Y which contains intrinsic tyrosine and/or tryptophan, nucleic acid or related fluorescence groups which are activated by wavelengths in the ultraviolet region, X and Y being in the relationship of antibody and antigen in that one has the ability to recognize the particular spatial and polar configuration of the other and is attracted and bound to such configuration, said beam of ultraviolet light being projected under such conditions that there is internal reflection at the said interface and the fluorescence can occur only within several thousand Angstroms of the surface, and than measuring the amount of fluorescence emitted from the surface of the interface, the amount of the fluorescence emission being a function of the amount of the unknown Y being detected.

The process of the invention is based on the principle that under conditions of internal reflection, fluorescent molecules within a few thousand Angstroms of the surface will be activated and fluoresce the number of molecules bound to the surface, and therefore, the number of fluorescent molecules of unknown in the assay solution can thus be measured.

By measuring the amount of fluorescence upon irradiation, one can obtain a determination of the presence of molecules having the same sites as the unknown molecules bound to the surface. By using standards having known amounts of such molecules, one can prepare a curve relating the amount of fluorescence to the amount of such molecules present in the assay medium.

The process of the invention is based on the fact that groups such as tyrosine and tryptophan units already present in the proteins, hormones, polynucleic acids, viruses, bacteria, or other microorganisms being assayed can be made to fluoresce by activation with light rays in the ultraviolet region, and as a result a reagent containing a fluorescence label need not be added to the assay solution. This presents several advantages over the known spectroscopic techniques in that it avoids the cost of adding the expensive secondary reagents containing the label, eliminating a washing step and avoids addition of label materials which can interfere with binding, particularly when dealing with the lower molecular weight hormones and drugs. Further advantage is also found in the fact that the process is interchangeable in that it can be used as a sensor for antigens based on the interaction between antigens and their immobilized antibodies at the solid-liquid interface, or as a sensor for antibodies based on the interaction between the antibodies and their immobilized antigens at the solid-liquid interface. The process of the invention can also be used to detect concentrations of unknown materials, such as drugs, which do not contain the fluorescent units tyrosine or trytophan. As noted below, this can be accomplished by addition of a second step wherein an antibody is added to the assay solution after the nonfluorescent unknown is bound.

Suitable apparatus which can be used to effect the process of the invention must be capable of internal reflection conditions and highly efficient in the transmission and detection of ultraviolet light. Suitable apparaus is that described in Kronick, et al.—U.S. Pat. No. 3,939,350, although considerable modification is required to use the ultraviolet msethod described herein. A suitable apparatus comprises a light source for the ultraviolet light, an optically transparent sheet to provide the interface in appropriate juxtaposition to provide internal reflection, a cell having the transparent sheet as one wall, and a light detector situated so as to receive fluorescent light from the cell.

DESCRIPTION OF THE DRAWINGS

FIG. 1 is a diagrammatic view of an immunoassay apparatus that can be used in the process of the invention.

FIG. 2 is a plot of the measured fluorescence intensity against time in an embodiment of the invention, wherein an antibody is immobilized at the solid-liquid interface and both the antibody and the antigen contain fluorescent tyrosine and/or tryptophan residues. In (A) we denote the presence of background fluorescence due to buffer or the medium of interest. As the antibody is introduced for the purposes of immobilization, an instantaneous increase in intensity is observed, followed by an increasing signal which relates to adsorption of the antibody at the solid surface. The signal B, therefore, is related to the amount of antibody immobilized to the surface. If one now introduces the antigen solution or the assay solution of interest at point C, there is a sharp increase in concentration due to the fluorescence of the antigen and related molecules in the excitation colume. This is followed by an increase to point D, which represents the proportion of antigen bound to the immobilized antibody. A wash initiated at the arrow at D results in the removal of the bulk solution fluorescence due to antigen and the steady state signal at the far right of the curve represents the amount of antigen, E, bound to the immobilized antibody. Thus, E, as indicated in the far right of the figure, is related to the concentration of bound antigen.

A similar experiment is an embodiment wherein the antigen is immobilized at the solid-liquid interface and its respective antibody in solution is the unknown.

FIG. 3

Another embodiment may be where the antigen, which is first immobilized, is non-fluorescent. No signal due to immobilized antigen is detected, but instead the background signal would continue up to the single arrow where the antibody is introduced. The double arrow at the right represents the amount of antibody bound to the non-fluorescent antigen.

Figure 2:
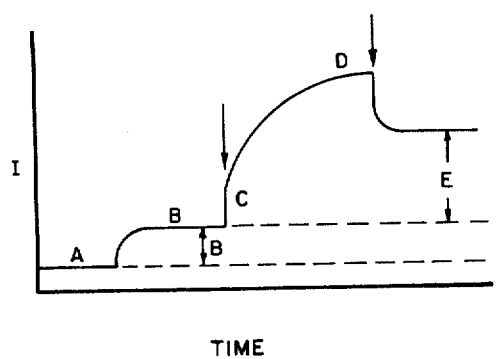
FIG. 2
Figure 3:
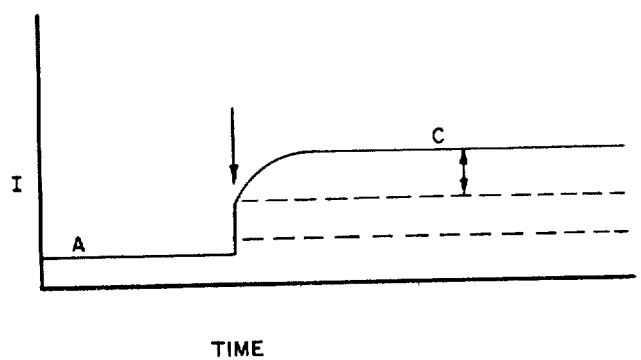

Many other variations on the theme shown in FIGS. 2 and 3 are, of course, evident.

Figure 1:
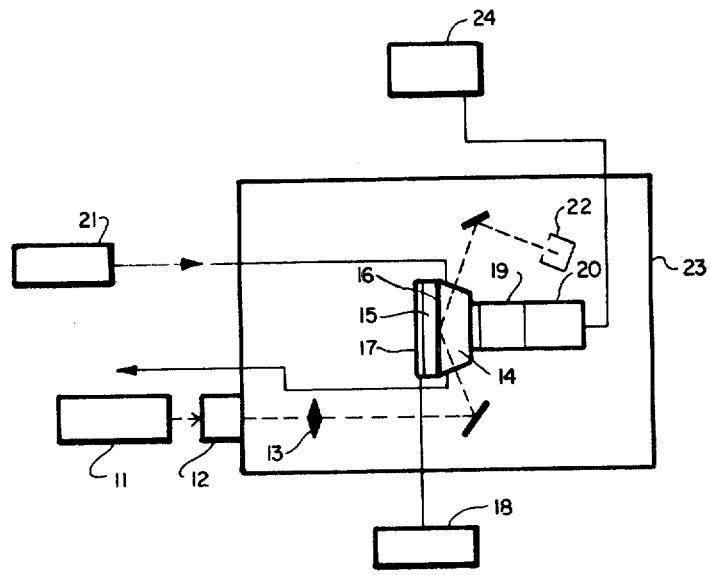
FIG. 1

As to FIG. 1, light source 11 is any source of ultraviolet light rays, such as a quartz-halogen lamp, mercury lamp, mercury-xenon lamp, or laser with UV output; 12 is a monochromator or filter which selectively passes the fluorescence excitation wavelengths; 13 is a quartz lens which collimates and reduces the beam diameter; 14 is a prism which is preferably a UV grade quartz with face angles of 70° to the base; 15 is a flow cell with means for introducing and withdrawing solution, and mounted on a suitable support such as a thick block of marine grade aluminum alloy anodized matt black after machining rectangular slit flow ports at the surface of each end, 16 is a gasket, preferably made of medical grade poly (dimethyl siloxane) to separate the flow cell and base and prism, 17 is a copper base plate to maintain the flow cell and solutions entering the cell at the constant temperature, preferably 30° C., and is attached to constant temperature bath 18; 19 is a monochromator or filter to receive the emission, and 20 is a photomultiplier tube linked to a photon counting system to quantify the fluorescence emissions; 21 is a syringe pump to maintain well-defined flow parameters; 22 is a beam stop to keep extraneous light signals at low level; 23 is a light tight housing to also help in keeping the extraneous light signals at a low level; 24 represents the photo counting electronics.

The light rays employed in the process of the invention are those in the ultraviolet region, and preferably those having wavelengths in the range of 2,000 to 4,000 Angstroms. A simple mercury-xenon lamp with interference filters to select the excitation wavelengths is a suitable source for the desired rays. A simple interference filter of monochromator can be used to select the fluorescence emission wave-lengths with a photomultiplier tube detection system. Laser and related light sources of the appropriate wave-lengths can also be used.

The reflecting element can be any conventional optical slab, prism, fiber or related optical element consistent with the total internal reflection requirement. A fiber optic can also be used directly as a sensing element as well as a means to direct the excitation light into the sensing region to the detector.

The more preferred sensing element is the conventional dovetail prism of FIG. 1. The prism employed can be of any ultraviolet transparent material, such as glass, quartz, alumina or sapphire, diamond, certain polyolefin plastics, e.g. poly-4-methyl-1-pentene, so long as it has the appropriate refractive index ratio with the surrounding less optically dense medium internal reflection. The optical materials must be highly pure and free of fluorescent additives and impurities.

As noted, the process of the invention depends upon internal reflection at a prism-aqueous buffer or prism-air interface. The basic methodology of internal reflection fluorescence spectroscopy is taught by Hirschfeld in U.S. Pat. No. 3,604,927 as a general analytical spectroscopic technique. Kronick, et al. U.S. Pat. No. 3,939,350 applies the Hirschfeld teaching to methods of fluorescence immunoassay but is limited to the use of light in the visible region of the spectrum as well as the need for adding labels to the reagents.

When using materials, such as prisms, as the reflection element, internal reflection can be obtained by controlling the angle at which the rays meet the prism. At an interface between two materials of different indicies, the angle of incidence is related to the angle of reflection by the following formula:

$$n_1 \sin \phi_1 = n_2 \sin \phi_2$$

wherein $n_1$ and $n_2$ are the refractive indicies of the two materials and $\phi_1$ and $\phi_2$ are the angles from the interface normal which the incident radiation makes at the interface. When the sine of the angles of incidence is equal to or greater than the ratio of the refractive indicies $n_2/n_1$, internal reflection occurs, and the light does not penetrate the second medium of lower refractive index.

Some light energy does in fact interact with the second medium over relatively short distances, usually not exceeding about 1,000 A for ultraviolet radiation. Depending upon variables involved, the distance of penetration of light energy can be diminished to less than 500 A. If a fluorescing molecule is positioned at the interface in the less dense medium, so as to be within the penetration depth into this medium, and if the wavelength of the light is within the adsorption peak of the fluorescing molecule, the molecule will fluoresce. Fluorescing molecules that are outside the narrow penetration depth are not excited and therefore, will not fluoresce.

In the preferred method of operating the process of the invention using the mercury-xenon lamp as noted above, and UV grade quartz prism, the rays are directed to the prism at an angle greater than 65° in order to obtain the desired total reflection with little penetration in the second medium.

Other optical geometries can be used to obtain internal reflection. This includes single and multiple reflection methods, (Harrick and Loeb, *Analytical Chemistry*, 45 (1973) 687) guided wave and integrated optic techniques, (J. F. Rabolt, et al. *Appl. Spect.*, 33 (1979) 549) fiber optic methods, (Hirschfeld, *Energy Tech. Rev.*, UCRL, 1980, p. 17 and R. E. Benner and R. K. Chang in *Fiber Optics*, ed., B. Bendow and S. S. Mitra, Plenum Press, 1979, p. 625) and/or plasmon resonance and/or microparticle enhancement as disclosed in (R. E. Benner, et al., *Optics Comm.*, 30 (1979) 145).

The materials to be immobilized on the prism surface, such as the antibodies or antigens, can be attached thereto by any known technique. The immobilization can be accomplished by adsorption from saline solution at a pH of about 6. After treatment, the prism surface is washed with water and rinsed with saline solution. In most cases, the bonding of the material, such as antibody or antigen to the surface is strong enough so that the assay can be carried out without significant desorption of the protein during the period of measurement.

After immobilization of the material on the prism as noted above, it is then brought in contact with the assay solution containing the unknown.

While it is preferred to use the surface of the prism as the interface or cell wall, it is also possible to and sometimes is more convenient to use a small disc or slide which may be optically coupled to the prism through a liquid of the same refractive index and mechanically held in position abutting the prism surface. The slide then serves as the interface between the assay medium and the surface at which total internal reflection occurs.

The assay solution containing the unknown is preferably an aqueous buffered solution having a pH range of about 6 to 9, and preferably between 7 and 8 and may include blood plasma, serum or other biological fluids.

The treatment of the prism to immobilize the X component as well as the introduction of Y into the cell are preferably accomplished at ambient temperature but higher or lower temperatures can be used as desired. As noted in the drawing FIG. 1, there is preferably a temperature bath employed to keep the temperature of the cell at about 30° C. to 40° C. and more preferably at about 37° C. Pressure employed in all cases is about atmosphere pressure although higher or lower pressures may be used as desired or needed.

In the present invention, the detection means is located so that substantially none of the exciting radiation, either directly or by scattering, is incident on the sensitive area of the detector, and substantially all radiation seen by the latter is induced fluorescence. The detector employed may be of any suitable construction as long as it permits measurment of the selected wavelength radiation being sent from the interface. Detection means such as a monochromator is capable of examining, through an input aperture, a selected wavelength within a particular spectral range. As shown in the attached drawing, a photomultiplier tube is linked to a photon system to quantify the fluorescence emissions.

The order of operation of the process of the invention may vary as needed according to the equipment selected. In general, the apparatus is assembled as shown in FIG. 1 with the light source turned on to determine the base line for the empty cell. The desired component X is then immobilized on the surface of the desired prism as by adsorption or by covalent immobilization, the treated prism is washed and rinsed and then introduced into the location near the assay cell as shown in the drawing. The base line for the prism interface without the unknown is then determined. The assay solution containing the unknown component Y is introduced into the cell and brought in contact with the prism interface and the base line determined. The solution is allowed to remain in contact with the interface until equilibrium is established. The fluorescent emissions are then determined by the use of the detector and the proper ratio determined to show the amount of the unknown Y in the assay solution.

The material to be assayed can be widely varied including naturally occurring and synthetic materials which may be high or low molecular weight and may be included in a variety of different liquid compositions or mixtures. Examples of such materials include the proteins, hormones, drugs of abuse, e.g. hypnotics and alkaloids, metabolites, particularly of diseased states, pesticides, vitamins, enzymes, viruses, bacteria, insulin, human chorionic gonadotrophin, CEA, angiotensin, and the like, synthetic drugs, such as methadone, amphetamine, and barbiturates, tri- or tetraiodothyronine, therapeutic drugs, e.g. antibiotics, diphenylhydrantoin glutethimide, primadone, and the like. Other examples include other haptens, and particularly those having a molecular weight of from about 125 to 1,000 and having from 1 to 8 heteroatoms, which are primarily oxygen, sulfur, nitrogen, phosphorus, alkali metal cations, e.g. sodium and potassium and halides. Other examples include the poly (amino acids) polypeptides and proteins—usually of from about 1,000 to 10⁶ molecular weight, which includes antigens, hormones, enzymes and the like.

Of special interest are the protein containing materials and preferably those containing at least one unit of tyrosine or tryptophan per molecule, and still more preferably those containing at least 1 unit of tryptophan per molecule.

DESCRIPTION OF SPECIFIC EMBODIMENTS

The process of the invention can be illustrated by the following specific embodiment utilizing only one step wherein an antibody is immobilized on the interface and the unknown is in the assay solution, both of which contain tyrosine and tryptophan units. The plot of the measured fluorescence in this case is shown in FIG. 2.

The signal without any fluorescent molecule present is shown in FIG. 2 as line A. When the prism is treated to immobilize human anti-gamma-globulin by adsorption from saline solution at pH 6, line B results. The treated prism was then exposed to solution containing gamma globulin and the fluorescence signal monitored (C). After equilibrium was reached, the signal was monitored and shown in the graph as line D. From the difference between lines C and D which represent the bound gamma globulin, the concentration of the gamma globulin in the assay solution is determined.

Another specific embodiment involves a one step process wherein an antigen is immobilized on the interface and the unknown antibody is contained in the assay solution with only the unknown containing the tyrosine and tryptophan fluorescence units. The plot of the measured fluorescence is shown in FIG. 3.

Since certain changes may be made in the above apparatus and processes without departing from the scope of the invention herein involved it is intended that all matter contained in the above description or shown in the drawing shall be interpreted as an illustration and not as placing a limit on the scope of the invention.

We claim:

1. A process for conducting fluorescence immunoassays without labels using internal reflection and wavelengths in the ultraviolet region which comprises directing a beam of light having wavelengths in the ultraviolet region to a solid-liquid interface which (i) has a material X immobilized thereon, and (ii) is in contact with an assay solution containing an unknown Y which contains at least one tyrosine, tryptophan, nucleic acid or other fluorescent group which is activated by wavelengths in the ultraviolet region, X and Y being in the relationship of antibody and antigen in that one has the ability to recognize the particular spatial and polar configuration of the other and is attracted to and bound to such configuration, said beam of ultraviolet light being projected under such conditions that there is internal reflection at the said interface, and then measuring the amount of fluorescence emitted from the surface of the interface, the amount of the fluorescence emission being a function of the amount of the unknown Y being detected.

2. A process as in claim 1 wherein X is an antibody and both X and Y contain at least one tyrosine, tryptophan or other fluorescent group which is activated by wavelengths in the ultraviolet region.

3. A process as in claim 1 wherein the X is an antigen and both X and Y contain at least one tyrosine, tryptophan or other fluorescent group which is activated by wavelengths in the ultraviolet region.

4. A process as in claim 1 wherein the antibody X is immobilized on the solid surface by physical adsorption.

5. A process as in claim 1 wherein the intrinsic absorption of tyrosine or tryptophan is in the range of 260 to 300 nanometers and fluorescence emission is collected in the range of 300 to 400 nanometers.

6. A process as in claim 1 wherein the intrinsic fluorescence is due to nucleic acids absorbing in the vicinity of 250 nanometers.

7. A process as in claim 1 wherein the kinetics of the adsorption and/or binding processes are monitored and the slopes of those kinetic curves used to determine affinity and binding constants and to determine concentrations in solution.

8. A process as in claim 1 wherein the assay solution is an aqueous solution.

9. A process as in claim 1 wherein the assay solution is blood serum, plasma, whole blood, or dilutions of blood, serum or plasma.

10. A process as in claim 1 wherein the X is anti-gamma-globulin.

11. A process as in claim 1 wherein the material Y to be assayed is an enzyme.

12. A process as in claim 1 wherein the X is an enzyme or enzyme complex.

13. A process as in claim 1 wherein the material Y to be assayed is a virus for which a specific antibody can be obtained.

14. A process as in claim 1 wherein the material Y to be assayed is a bacterium or other microorganism.

15. A two step process for conducting fluorescent immunoassays without labels using internal reflection, wavelengths in the ultraviolet region and directed to the determination of an unknown material which does not contain tyrosine or tryptophan fluorescence groups, which comprises directing a beam of light having wavelengths in the ultraviolet region to a solid-liquid interface which (1) has a material X immobilized thereon, and (2) has been contacted with an aqueous solution containing the unknown material and with a second solution containing Y which contains at least one tyrosine or tryptophan fluorescence group which is activated by wavelengths in the ultraviolet region, X and Y being either antibody or antigen in relation to the unknown material, said beam of ultraviolet light being projected under such conditions that there is internal reflection at the said interface and then measuring the amount of fluorescence emitted from the surface of the interface, the amount of the fluorescent emission being a function of the amount of unknown being detected.

16. A process as in claim 15 wherein the unknown is a drug.

17. A process as in claim 15 wherein the unknown is a hormone free of tyrosine and/or tryptophan.

18. A process as in claim 15 wherein the unknown is any chemical for which a specific antibody or specific receptor can be obtained.

19. A process as in claim 15 wherein the reaction at the interface is conducted at a temperature of 1° C. to 75° C. and at a residence time of 1 nanosecond to 60 minutes.

20. A process as in claims 1 or 19 wherein the interfacial excitation is enhanced by plasmon resonances and/or microparticle resonances.

* * * * *